(12) United States Patent
Xiao et al.

(10) Patent No.: US 9,555,402 B2
(45) Date of Patent: Jan. 31, 2017

(54) PROCESS FOR PREPARING ZEOLITE BETA AND USE THEREOF

(71) Applicant: SHELL OIL COMPANY, Houston, TX (US)

(72) Inventors: Fengshou Xiao, Hangzhou (CN); Xiangju Meng, Hangzhou (CN); Jie Zhu, Hangzhou (CN)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 14/650,692

(22) PCT Filed: Dec. 10, 2013

(86) PCT No.: PCT/EP2013/076098
§ 371 (c)(1),
(2) Date: Jun. 9, 2015

(87) PCT Pub. No.: WO2014/090808
PCT Pub. Date: Jun. 19, 2014

(65) Prior Publication Data
US 2016/0184808 A1  Jun. 30, 2016

(30) Foreign Application Priority Data
Dec. 10, 2012 (CN) .......................... 2012 1 0529722

(51) Int. Cl.

| | | |
|---|---|---|
| C07C 45/00 | (2006.01) |
| C07C 37/00 | (2006.01) |
| C07C 39/00 | (2006.01) |
| B01J 29/00 | (2006.01) |
| B01J 35/00 | (2006.01) |
| C01B 39/00 | (2006.01) |
| B01J 29/70 | (2006.01) |
| C10G 1/10 | (2006.01) |
| C07C 2/86 | (2006.01) |
| C01B 39/48 | (2006.01) |
| B01J 37/00 | (2006.01) |
| B01J 37/10 | (2006.01) |
| C07C 37/16 | (2006.01) |
| C07C 45/72 | (2006.01) |

(52) U.S. Cl.
CPC ......... B01J 29/7007 (2013.01); B01J 37/0018 (2013.01); B01J 37/10 (2013.01); C01B 39/48 (2013.01); C07C 2/864 (2013.01); C07C 37/16 (2013.01); C07C 45/72 (2013.01); C10G 1/10 (2013.01); *C07C 2529/70* (2013.01)

(58) Field of Classification Search
CPC .......... C07C 45/74; C07C 39/06; C07C 37/16; C07C 15/16; C07C 2/66; B01J 29/041; B01J 29/7007; B01J 35/002; C01B 39/48
See application file for complete search history.

(56) References Cited

FOREIGN PATENT DOCUMENTS

CN         1749162         3/2006

OTHER PUBLICATIONS

Wang, L., et al.; "Hierarchial mesoporous zeolites with controllable mesoporosity templated from cationic polymers"; Microporous and Mesoporous Materials, Elsevier Science Publishing; vol. 131, No. 1-3; pp. 58-67; Jun. 1, 2010.
Moller et al.; "Hierarchical Zeolite Beta via Nanoparticle Assembly with a Cationic Polymer", Chemistry of Materials, vol. 23, No. 19, Oct. 11, 2011 (Oct. 11, 2011), pp. 4301-4310, XP055097558, ISSN: 0897-4756, DOI: 10.1021/cml03533ecolumn I, line 1—col. III, line 44 col. IV, line 59—col. XIV, line 15.
Feng-Shou, et al.; : "Catalytic Properties of Hierarchical Mesoporous Zeolites Tempiated with a Mixture of Small Organic Ammonium Salts and Mesoscale Cationic Polymers", Angewandte Chemie International Edition, vol. 45, No. 19, May 5, 2006 (May 5, 2006), pp. 3090-3093, XP055097869, ISSN: 1433-7851, DOI: 10.1002/anie.200600241 the whole document.
Meng et al.; : "Tempiating route for synthesizing mesoporous zeolites with improved catalytic properties", Nano Today, Elsevier, Amsterdam, NL, vol. 4, No. 4, Aug. 1, 2009 (Aug. 1, 2009), pp. 292-301, XP026349289, ISSN: 1748-0132[retrieved on Jun. 30, 2009] col. XI, line 10—col. XIV, line 30.
Liu et al.; "Preformed zeolite precursor route for synthesis of mesoporous X zeolite", Colloids and Surfaces. A, Physicachemical and Engineering Aspects, Elsevier, Amsterdam, NL, vol. 318, No. 1-3, Jan. 6, 2008 (Jan. 6, 2008), pp. 269-274, XP022523916, ISSN: 0927-7757, DOI: 1O.1016/J.COLSURFA.2OO8.O1.O02 col. III, lines 21-55.
Shiju et al.; ; "Recent developments in catalysis using nanostructured materials", Applied Catalysis A: General, Elsevier Science, Amsterdam, NL, vol. 356, No. 1, Mar. 1, 2009 (Mar. 1, 2009) , pp. 1-17, XP025913211, ISSN: 0926-860X, DOI: 10.1016/J.APCATA.2OO8.11.034 [retrieved on Dec. 14, 2008] the whole document.

*Primary Examiner* — Sikarl Witherspoon
(74) *Attorney, Agent, or Firm* — Charles W. Stewart

(57) ABSTRACT

Method for preparing zeolite beta which method comprises crystallization of zeolite beta from a solution comprising a template, a silicon source and an aluminum source in which the template is polymeric compound comprising ionizable polydiallyldimethylammonium (PDADMA) cationcrystallization. Furthermore, the present invention provides the use of thus prepared zeolite beta in catalysts for hydrocarbon conversions.

20 Claims, 3 Drawing Sheets

US 9,555,402 B2

PROCESS FOR PREPARING ZEOLITE BETA AND USE THEREOF

PRIORITY CLAIM

The present application is the National Stage (§371) of International Application No. PCT/EP2013/076098, filed Dec. 10, 2013, which claims priority from Chinese Patent Application No. 201210529722.7, filed Dec. 10, 2012, incorporated herein by reference.

FIELD OF THE INVENTION

The present invention is related to a novel method for preparing zeolite beta, more specifically zeolite beta having a composite pore structure, and further to the use of the zeolite beta so prepared in catalysts for hydrocarbon conversions.

BACKGROUND OF THE INVENTION

In the art of zeolites, zeolite with a composite pore structure means that the zeolite has incorporated a further pore structure beyond its original pore structure so that to have a composite pore structure, thereby the zeolite has a varied pore structure and improved porosity as well as varied mass transfer ability and catalytic activity.

Since MCM-41 zeolite molecular sieve with a composite pore structure was synthesized by Mobil Company from USA in 1992 and the same was found to be with an ability of quickly mass transferring and high catalytic activity for hydrocarbon conversions [cf. Kresge, C. T., Leonovicz, M. E., Roth, W., J., Vartuli, J. S. Nature 353, (1992), 710.], the zeolite with a composite pore structure has received more and more attention and there are more and more zeolites being imparted with composite pore structures successfully, thereby zeolites being imparted with more possibility for extensive industrial uses.

Zeolite beta with a composite pore structure is such a zeolite, whereinto a meso-pore structure is incorporated beyond its original micro-pore structure, so that zeolite beta has a composite pore structure comprising both micro-pore structure and meso-pore structure simultaneously, thereby zeolite beta has improved mass transfer efficiency and catalytic activity for hydrocarbon conversions.

Ryoo et al. have developed a bifunctional surfactant for synthesizing zeolite comprising both mesopore and micropore simultaneously, thereby yielding zeolite nanosheets or mesoporous zeolites. However, said bifunctional surfactant is costly so that its industrial applications are less feasible. Thus, there is still need to improve the synthesis of zeolite beta with a composite pore structure in the art.

In order to make zeolite beta with a composite pore structure could be used commercially, in Chinese patent application CN 1749162A, the present inventors have successfully synthesized zeolite beta with a composite pore structure by using a combination of polyquaternium-6 (polydiallyldimethylammonium chloride) and TEAOH (tetraethylammonium hydroxide) as templates (cf. example 2 and FIGS. 8-9 therein).

According to such a synthesis route, based on the conventional concepts in the art, of the combined templates, the organic small molecular template, i.e. tetraethylammonium hydroxide (TEAOH), is used to form the microporosity, and the organic high molecular template, i.e. polyquaternium-6, is used to form the mesoporosity. Thus, the two organic templates have to match with each other very well, otherwise, some amorphous porous materials could be easily formed in the synthesized zeolite. Thus, such combined templates make the synthesis of zeolite beta with a composite pore structure little complicated, although the same had been more feasible than that by Ryoo et al. for commercial applications already.

With such a situation, the present inventors now have surprisingly found that zeolite beta with beneficial properties, more specifically zeolite beta having a composite pore structure, can be successfully synthesized by using a polymeric compound comprising ionizable polydiallyldimethylammonium (PDADMA) cation such as polyquaternium-6 as the only template present during its preparation. Viewing that such a polymeric compound such as polyquaternium-6 is much cheaper than TEAOH as commercial agents, the present invention makes the synthesis of zeolite beta with a composite pore structure more simplified with reduced cost, thus, promoting zeolite beta with a composite pore structure to be used in extensive industrial applications.

SUMMARY OF THE INVENTION

Thus, the present invention provides a method for preparing zeolite beta, more specifically zeolite beta having a composite pore structure. This method may be carried out by conventional hydrothermal synthesis, but instead of the combined templates in the prior art, only single kind of template is present during its manufacture which results in a zeolite beta having beneficial properties more specifically zeolite beta having a combined micro-pore structure and meso-pore structure of the composite pore structure of zeolite beta.

Specifically, the present invention provides a method for preparing zeolite beta, which method comprises crystallization of zeolite beta from a solution comprising a template, a silicon source and an aluminum source in which the template is polymeric compound comprising ionizable polydiallyldimethylammonium (PDADMA) cation. More specifically, the preparation process is a hydrothermal crystallization using PDADMA as the template, and wherein the molar ratio $SiO_2$/PDADMA between the silicon source calculated as $SiO_2$ and the polymeric compound calculated as the cationic PDADMA monomer is of 1-10, preferably of 3-8, and most preferably of 5-7, the molar ratio $SiO_2/M_2O$ between the silicon source calculated as $SiO_2$ and the base source calculated as alkali metal oxide $M_2O$ is of 1-10, preferably of 3-8, and most preferably of 4-6. This preparation process preferably is carried out under a temperature of 150-230° C., preferably of 170-200° C. for a time period of 48-312 h, preferably of 60-240 h and most preferably of 72-120 h.

According to the present invention, wherein the aluminum source and the water may be used at conventional amounts in the art, however, it is preferred that the molar ratio $SiO_2/Al_2O_3$ between the silicon source calculated as $SiO_2$ and the aluminum source calculated as $Al_2O_3$ is of 20-100, preferably of 30-80, and most preferably of 40-55, and the molar ratio $H_2O/SiO_2$ between the water and the silicon source calculated as $SiO_2$ is of 10-80, preferably of 25-65, and most preferably of 40-50.

According to the present invention, wherein the hydrothermal crystallization may be carried out conventionally, specifically may be carried out by mixing, gelling and crystallizing sequentially. More specifically, according to the present invention, during the hydrothermal crystallization, firstly dissolving the aluminum source and the base source in the water, adding the polymeric PDADMA compound and stirring for a time period of 0.2-1.5 h, preferably of 0.3-1.0 h to form a clear solution; adding the silicon source to the solution and stirring for a time period of 6-48 h, preferably of 12-24 h to form a gel; and transferring the gel into an autoclave to be crystallized.

According to the present invention, wherein after the hydrothermal crystallization, the resultant product may be conventionally processed to obtain the final zeolite beta with a composite pore structure. Specifically, according to the present invention, the product obtained by hydrothermal crystallization may be filtered, dried and calcined sequentially. More specifically, the product obtained by hydrothermal crystallization may be filtered at a temperature from ambient temperature to 40° C., preferably from ambient temperature to 30° C., dried at a temperature of 80-120° C., preferably of 90-110° C., and calcined at a temperature of 400-700° C., preferably of 500-600° C. for a time period of 3-10 h, preferably of 4-8 h.

According to the present invention, wherein the silicon source may be any silicon source conventionally used in the art, specifically, the silicon source may be selected from the group consisting of silica such as silica gel, silica sol, quartz, white carbon black and clay; silicic acid; silicate esters such as methyl silicate, ethyl silicate and propyl silicate; and silicate salts such as sodium silicate, potassium silicate and aluminum silicate.

According to the present invention, wherein the aluminum source may be any aluminum source conventionally used in the art, specifically, the aluminum source may be selected from the group consisting of aluminate salts such as sodium aluminate and potassium aluminate; aluminum salts such as aluminum isopropoxide, aluminum silicate, aluminum sulfate, aluminum nitrate and aluminum chloride; aluminum minerals such as boehmite and pseudo-boehmite; and aluminum.

According to the present invention, wherein the base source may be any base source conventionally used in the art, specifically, the base source may be selected from alkali and alkali earth metal oxide, hydroxide, carbonate and bicarbonate, preferably from alkali metal oxide, hydroxide, carbonate and bicarbonate, particularly from sodium oxide, potassium oxide, sodium hydroxide, potassium hydroxide, sodium carbonate, potassium carbonate, sodium bicarbonate and potassium bicarbonate, and most preferably from sodium hydroxide and potassium hydroxide.

According to the present invention, sodium silicate and sodium aluminate may be used as the base source either. Thus, according to the present invention, sodium silicate may be used as the silicon source and the base source simultaneously and sodium aluminate may be used as the aluminum source and the base source simultaneously.

The polymeric compound comprising ionizable polydiallyldimethylammonium (PDADMA) cation is a compound which is able to provide a PDADMA cation. This polymeric compound is thought to provide the composite pore structure during the synthesis of the zeolite. According to the present invention, the template can be any polymeric compound capable of providing PDADMA cation during the synthesis of the zeolite. Herein, the polymeric compound refers to the compound comprising polymeric cation and small anion, more specifically to the compound comprising PDADMA cation and small anion, which is referred as polymeric PDADMA compound for short.

According to the present invention, wherein the templating polymeric PDADMA compound may be used at the conventional molecular weight range in the art, specifically, the PDADMA salt may be with a molecular weight of $1 \times 10^5$-$5 \times 10^5$, preferably of $1 \times 10^5$-$3 \times 10^5$, and most preferably of $1 \times 10^5$-$2 \times 10^5$.

According to the present invention, the examples of the templating polymeric PDADMA compound may comprise PDADMA salt or hydroxide, with PDADMA salt being preferred, and the PDADMA salt may be PDADMA halide, preferably PDADMA chloride, PDADMA bromide and PDADMA iodide, and most preferably PDADMA chloride.

According to the present invention, wherein the template, when being PDADMA salt, may be provided in the form of aqueous solution with a solid content of 10-60 wt %, and preferably of 15-45 wt %.

Without wishing to be bound by any particular theory, the inventors believe that under particular synthesis conditions, during the formation of the composite pore structure of zeolite beta, the small quaternary ammonium head of cationic PDADMA may direct the formation of the micro-pores because the similar small quaternary ammonium cations are general templates for the synthesis of conventional zeolite beta, and the cationic PDADMA moiety with relatively large molecular weight may direct the formation of the meso-pores. Thus, such a templating polymeric compound with a particular quaternary ammonium head has both functions of forming micro-pores and meso-pores simultaneously, and is similar to Ryoo et al.'s delicated surfactant, but of significantly reduced cost. Furthermore, using templating polymeric PDADMA compound only is more simple than the combined templates in the inventor's previous Chinese patent specification CN 1749162A.

According to the present invention, the synthesized zeolite beta has improved properties. Specifically, compared with the conventional zeolite beta, the presently synthesized zeolite beta has comparable ratio Si/Al, much higher BET surface and much higher pore volume as well as excellent hydrothermal stability, all of these properties are very critical for zeolite beta to be used in industrial applications.

Herein, the inventors have found that zeolite beta according to the present invention is especially suitable for use in catalysts for hydrocarbon conversions, specifically, such zeolite beta can be used not only in catalysts for hydrocracking light hydrocarbons, but also in catalysts for conversion of bulky molecular hydrocarbons due to its particularly high specific surface area and high pore volume.

Accordingly, the present invention also provides a hydrocarbon conversion catalyst comprising the presently synthesized zeolite beta. More specifically, the hydrocarbon conversion catalyst comprises 5-95 wt % of refractory oxide binder, 5-95 wt % of zeolite beta prepared according to the present invention, and 0.01-30 wt % of catalytically active metals, all the percentages being based on total amount of dry catalyst.

Regarding the hydrocarbon conversion catalyst of the present invention, the binder can be any refractory oxide. Preferably, the binder is chosen from the group consisting of silica, alumina, silica-alumina and titania. The catalytically active metals preferably are chosen from the group consisting of molybdenum, tungsten, nickel, cobalt, platinum and palladium.

The hydrocarbon conversion catalyst of the present invention can be prepared in any way known to be suitable to someone skilled in the art such as by co-mulling and extrusion. Preferably, the catalyst is prepared by co-mulling or by extrusion of zeolite beta prepared according to the present invention and binder with subsequent impregnation of the extrudates with a solution containing the catalytically active metals. The final catalyst is obtained by subsequent drying, calcining and optionally sulfiding.

The present invention further provides a process for hydrocracking hydrocarbons by contacting the hydrocarbon feedstock with hydrogen at elevated temperature and elevated pressure in the presence of the hydrocarbon conversion catalyst of the present invention. Examples of such processes comprise single-stage hydrocracking, two-stage hydrocracking, and series-flow hydrocracking.

According to the present invention, the hydrocracking process may be conveniently carried out at a reaction temperature of 250-500° C. and a total pressure (at the reactor inlet) of $3 \times 10^6$ to $3 \times 10^7$ Pa, more preferably of $8 \times 10^6$ to $2.0 \times 10^7$ Pa. Where a hydrocracking process is carried out at a low pressure of, for example, up to $1.2 \times 10^7$ Pa, this may be termed 'mild hydrocracking'.

Hydrocarbon feeds which can be useful in the present process can vary within a wide boiling range. They include atmospheric gas oils, coker gas oils, vacuum gas oils, deasphalted oils, waxes obtained from a Fischer-Tropsch synthesis process, long and short residues, catalytically cracked cycle oils, thermally or catalytically cracked gas oils, and syncrudes, optionally originating from tar sand, shale oils, residue upgrading processes and biomass. Combinations of various hydrocarbon oils may also be employed. Typically, though, the feedstocks most suited for the process of the invention are the lighter feedstocks or fractions obtained by treatment of a feedstock through cracking or fractionation. Such feedstocks include atmospheric and vacuum gas oils, gas oils formed by cracking processes, cycle oils, and similar boiling range feedstocks. The boiling range of the feedstocks will generally be of the order of 90-650° C.

Furthermore, the present invention is also related to bulky molecular hydrocarbon conversions by use of the presently synthesized zeolite beta, said bulky molecular hydrocarbon conversions comprise pyrolysis of polyethylene, alkylation of benzene with benzyl alcohol (ABB), condensation of benzaldehyde with hydroxyacetophenone (CBH), and alkylation of phenol with tert-butyl alcohol (APT).

Regarding the bulky molecular hydrocarbon conversions, the presently synthesized zeolite beta can reach much higher catalytic activity and conversion than that by conventional zeolite beta. For example, for LDPE pyrolysis over the two zeolites, when the conversion is of 10% and 50%, the pyrolysis temperature for the presently synthesized zeolite beta is lower than that for conventional zeolite beta by 60° C. and 23° C. respectively, and it is thought that such an improvement is due to the presence of the meso-pores in the presently synthesized zeolite beta with a composite pore structure (cf. FIG. 4).

BRIEF DESCRIPTION OF THE DRAWINGS

Now the present invention is further described with reference to the figures, wherein:

FIG. 3a-3d shows TEM images of the zeolite product synthesized by the present invention, wherein FIGS. 3a and 3b are low magnification images, FIGS. 3c and 3d are high resolution images, and the inserted at left bottom of FIG. 3b is an electron diffraction image of zeolite particle;

DETAILED DESCRIPTION OF THE INVENTION

Figures 1, 2:
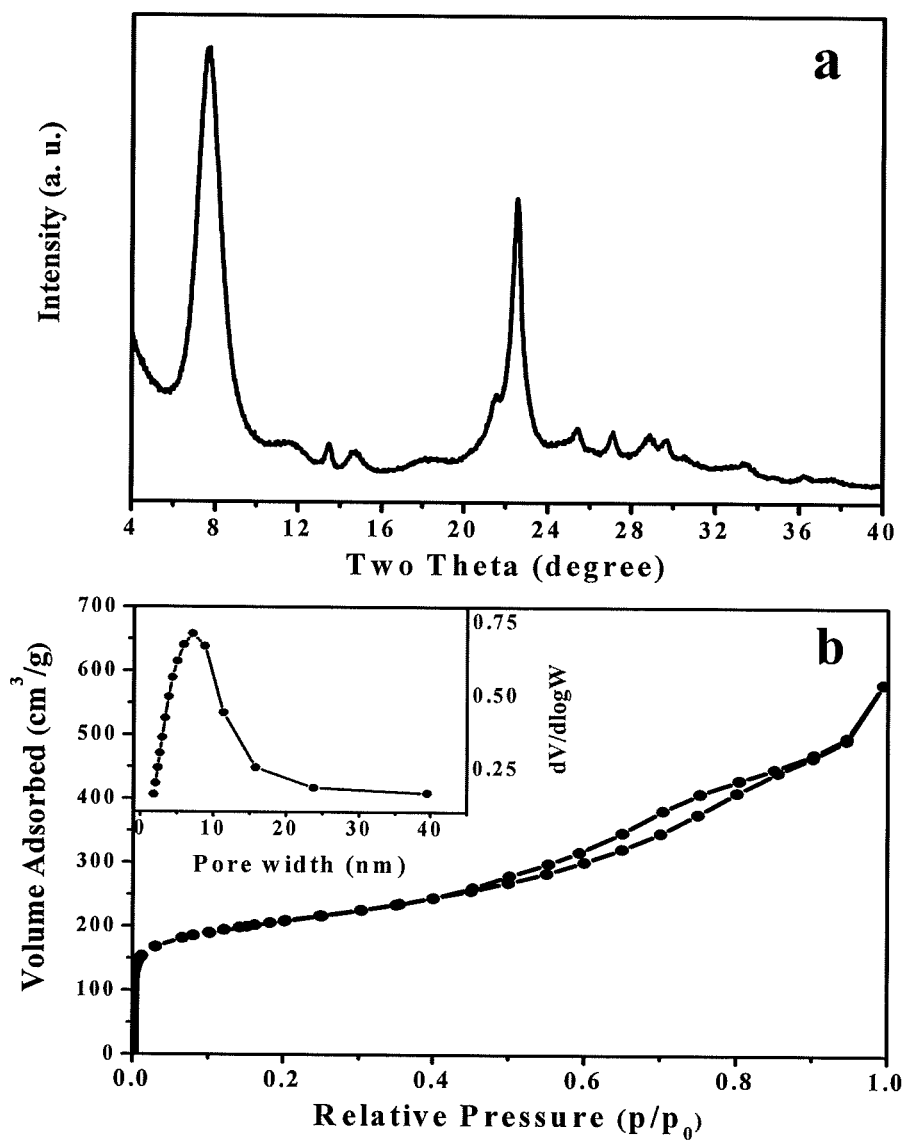
FIG. 1 shows X-ray diffraction (XRD) spectra of the zeolite product synthesized by the present invention.
FIG. 2 shows isothermal nitrogen absorption-desorption curves of the zeolite product synthesized by the present invention.

In the present invention, the following measurements are involved:

Ratio Si/Al was determined by a PW1400 X ray fluorescence spectrometer XRF analysis;

XRD spectra were measured by a Rigaku X-ray diffractometer using Cu Kα ($\lambda$=1.5418 Å) radiation; Isothermal nitrogen absorption-desorption curves were measured at −196° C. using a Micromeritics ASAP 2020M and 3020M system, wherein the sample was degassed for 10 h at 150° C. before being measured;

TEM images were obtained on a JEOL JEM-2100F electron microscope operated at 200 kV and JEOL JEM-3010 instrument operated at 300 kV;

Pore size distribution for mesopores was calculated using Barrett-Joyner-Halenda (BJH) model; and Thermogravimetric analysis (TG) and differential thermal analysis (DTA) were performed with SDT Q600 V8.2 Build 100 instrument in air with a heating rate of 10° C./min.

Now the present invention is described by reference to a specific example, which is provided to demonstrate the present invention only, rather than to limit the present invention in any way.

Example

In this example, all the reaction agents are of technical grade, wherein:

The template is polydiallyldimethylammonium chloride (aqueous solution with a solid content of 20 wt % and a molecular weight of $1 \times 10^5$-$2 \times 10^5$) purchased from Sigma-Aldrich Company, Ltd. (USA);

The silica source is fumed silica purchased from Shenyang Chemical Co.;

The base source is NaOH and the aluminum source is $NaAlO_2$, both of them were purchased from Sinopharm Chemical Reagent Co.;

Benzene, benzyl alcohol, benzaldehyde, 2-hydroxyacetophenone, phenol, tert-butyl alcohol and dodecane were purchased from Aladdin Industrial Co (China); and Low-density polyethylene (LDPE) was purchased from Alfa Aesar.

Synthesis of Zeolite Beta with a Composite Pore Structure

In this example, single crystals of zeolite beta according to the invention were synthesized by use of PDADMA chloride as template, wherein the silicon source calculated as $SiO_2$, the template calculated as cationic PDADMA monomer, the aluminum source calculated as $Al_2O_3$, the base source calculated as $Na_2O$ and $H_2O$ were used at a molar ratio of $45SiO_2/7.5PDADMA/Al_2O_3/10Na_2O/2258H_2O$.

Specifically, 0.08 g $NaAlO_2$ and 0.3 g NaOH being dissolved in 12.1 mL deionized water, then 2.0 g PDADMA chloride (calculated on the basis of the aqueous solution with a solid content of 20 wt %) being added and stirring being continued for about 0.5 h to form a clear solution; then, 0.935 g fumed silica being added to the clear solution and stirring being continued for 12-24 h to form a gel; and the resultant gel being transferred into an autoclave to be crystallized at about 180° C. for about 96 h; finally, the resultant crystallization product being filtered at room temperature, dried at about 100° C., and calcined at about 550° C. for about 5 h to remove the template, thereby the zeolite product beta-MS being obtained.

Characterization, Confirmation and Properties of the Product

The zeolite product beta-MS was measured for XRD spectra, isothermal nitrogen absorption-desorption curves and TEM images respectively. Specifically:

XRD spectra are shown in FIG. 1. It can be seen that the shown spectra are of typical zeolite beta, thus, it can be confirmed that the presently synthesized product is zeolite beta indeed;

Isothermal nitrogen absorption-desorption curves are shown in FIG. 2. It can be seen that the isothermal nitrogen absorption-desorption curves exhibit a hysteresis loop at a relative pressure of $0.50<P/P_0<0.90$, thereby the presence of meso-pores in the presently synthesized zeolite beta can be confirmed.

Figures 3A, 3B, 3C, 3D:
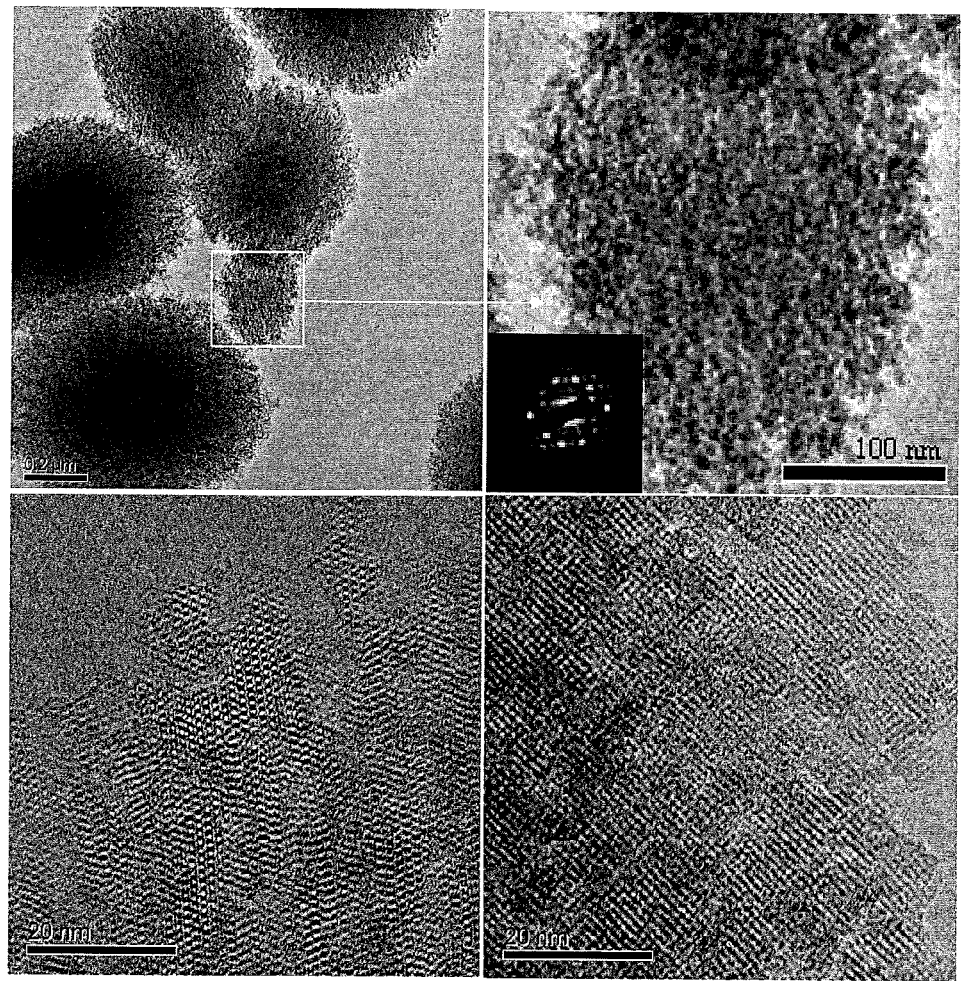

TEM images are shown in FIG. 3a-3d, wherein low magnification images (FIGS. 3a and 3b) show obvious mesopores in the sample, thus it is further confirmed that the presently synthesized zeolite beta is with a composite pore structure; and wherein high resolution TEM images (FIGS. 3c and 3d) show very ordered micropores in same direction and this is in good agreement with the characteristics of single crystals of zeolite beta, thereby it is determined that the presently synthesized zeolite beta with a composite pore structure is its single crystals, furthermore, this regard can be demonstrated by that the electron diffraction of zeolite beta particle, inserted at left bottom of FIG. 3b, is a single set of diffraction spectra, which indicated that zeolite beta particle is a single crystal rather than a nanocrystal aggregation.

Finally, for the presently synthesized zeolite beta with a composite pore structure, the following properties, i.e. ratio Si/Al of 10.2, BET surface area of 724 m²/g, pore volume of 0.90 cm³/g, and the calculated central value of BJH pore size distribution of 7 nm, were obtained through further analyses and measurement.

Test of Hydrothermal Stability

After being exposed to 100% steam at 700° C. for 2 h, the synthesized zeolite product beta-MS has BET surface area of 538 m²/g, pore volume of 0.87 cm³/g, and the calculated central value of BJH pore size distribution of 11.4 nm. Compared with the above-mentioned original data, it can be known that the presently synthesized zeolite beta-MS with a composite pore structure has good hydrothermal stability, i.e. keeping high BET surface area and large pore volume even after hydrothermal treatment. Thus, the presently synthesized zeolite beta with a composite pore structure has a good properties for industrial applications.

Test of Catalytic Ability

The presently synthesized zeolite beta MS with a composite pore structure is tested for its catalytic ability in comparison with the conventional zeolite beta, which conventional zeolite beta was purchased from Nankai University and is with ratio Si/Al of 12.2, BET surface area of 587 m²/g and pore volume of 0.36 cm³/g, and after hydrothermal treatment, i.e. after being exposed to 100% steam at 700° C. for 2 h, is with BET surface area of 487 m²/g and pore volume of 0.36 cm³/g, that is to say, this conventional zeolite beta is with good hydrothermal stability and suitable for industrial application either. Table 1 shows a summary about the properties of the presently synthesized zeolite beta MS with a composite pore structure and the conventional zeolite beta before and after hydrothermal treatment.

TABLE 1

| Zeolites | | BET surface area (m²/g) | Total pore volume (m³/g) |
|---|---|---|---|
| beta MS (presently synthesized, Si/Al = 10.2) | Before hydrothermal treatment | 724 | 0.90 |
| | After hydrothermal treatment | 538 | 0.87 |
| beta (conventional, Si/Al = 12.2) | Before hydrothermal treatment | 587 | 0.36 |
| | After hydrothermal treatment | 480 | 0.36 |

All the zeolite samples used in the tests of catalytic ability are in hydrogen form. For this purpose, the zeolite samples were ion-exchanged with 1M $NH_4NO_3$ at 80° C., then calcined at 500° C. for 5 h, and this procedure was repeated twice, thereby both zeolite beta MS with a composite pore structure and the conventional zeolite beta in hydrogen form were obtained.

Herein, the obtained zeolite beta MS with a composite pore structure and the conventional zeolite beta in hydrogen form were used in bulky molecular hydrocarbon conversions such as low-density polyethylene (LDPE) pyrolysis, alkylation of benzene with benzyl alcohol (ABB), condensation of benzaldehyde with hydroxyacetophenone (CBH), and alkylation of phenol with tert-butyl alcohol (APT).

Figure 4:
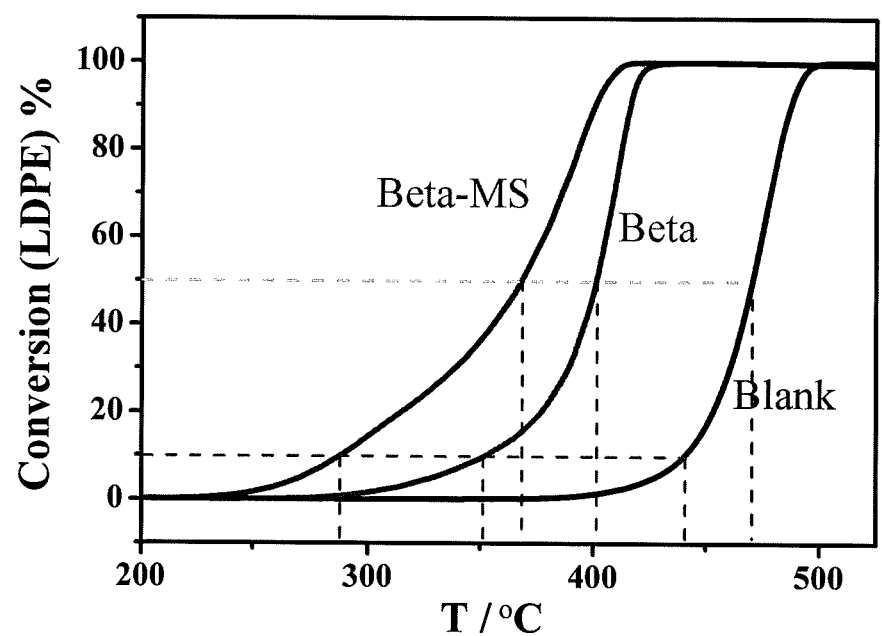
FIG. 4 shows the curves for conversions versus temperatures of PDPE pyrolyses over beta MS (zeolite beta according to the present invention) and beta (conventional zeolite beta) as well as without any catalyst (blank), wherein the conversions are determined from thermogravimetric data.

Firstly, low-density polyethylene (LDPE) pyrolysis was carried out in a HENVEN HCT-3 (Beijing) differential thermal balance under a nitrogen flow of 50 cm³/min and a reaction temperature ramping from 30° C. to 600° C. at a rate of 10° C./min, wherein the polymer powder and the zeolite were carefully weighed and intimately mixed at a mass ratio 10:1 in the $\alpha$-$Al_2O_3$ crucibles of the differential thermal balance. FIG. 4 shows the curves for conversions versus temperatures of PDPE pyrolyses over beta MS (zeolite beta with a composite pore structure) and beta (conventional zeolite beta) as well as without any catalyst (Blank), wherein the conversions are determined from thermogravimetric data of LDPE.

As can be known from FIG. 4, the presently synthesized zeolite beta MS with a composite pore structure has much higher catalytic activity than the conventional zeolite beta, specifically, zeolite beta MS with a composite pore structure can reach a relatively high conversion at a relatively low reaction temperature. Of course, both zeolite beta MS and zeolite beta show significant catalytic activity over that without any catalyst (shown as Blank in FIG. 4).

Furthermore, in alkylation of benzene with benzyl alcohol (ABB), condensation of benzaldehyde with hydroxyacetophenone (CBH), and alkylation of phenol with tert-butyl alcohol (APT) (their reaction formula are shown in FIG. 5), the obtained products were analyzed by gas chromatography Shimazu 2010C with a flame ionization detector (FID), wherein a column DB-1 (30 m) was used, the flame ionization detector (FID) is at a temperature of 280° C., and the separated product was determined by $^1$H NMR technology.

All the above-mentioned three reactions are carried out in a three-necked round flask equipped with a condenser and a magnetic stirrer, wherein the reaction temperature is ramping from an initial value of 80° C. to a final value of 280° C. at a heating rate of 10° C./min. In all the three reactions, a stirring rate of higher than 800 rpm and catalyst particles smaller than 400 mesh were required.

Specifically, the alkylation of benzene with benzyl alcohol (ABB) was carried out by mixing 0.02 g catalyst with 57 mmol benzene and 2.9 mmol benzyl alcohol at about 80° C. for a time period of about 5 h; the condensation of benzaldehyde with 2-hydroxyacetophenone (CBH) was carried out by mixing 0.10 g catalyst with 14 mmol benzaldehyde and 7 mmol 2-hydroxyacetophenone at about 150° C. for a time period of about 18 h; and the alkylation of phenol with tert-butyl alcohol (APT) was carried out by mixing 0.15 g catalyst with 5 mmol phenol, 10 mmol tert-butyl alcohol, and 10 ml cyclohexane solvent at about 100° C. for a time period of about 4 h.

The conversions of each reaction over the two catalysts are shown in Table 2.

TABLE 2

| Zeolites | Conversions of each reaction (%) | | |
|---|---|---|---|
| | ABB | CBH | APT |
| Zeolite beta MS (Si/Al = 10.2) | 48 | 59 | 61 |
| Zetolite beta (comprative, Si/Al = 12.2) | 27 | 35 | 44 |

As can be known from the data in table 2, in terms of alkylation of benzene with benzyl alcohol (ABB), condensation of benzaldehyde with hydroxyacetophenone (CBH), and alkylation of phenol with tert-butyl alcohol (APT), the presently synthesized zeolite beta MS with a composite pore structure reached much higher conversions than the conventional zeolite beta.

Thus, the presently synthesized zeolite beta with a composite pore structure is much better than the conventional zeolite beta when being used as the catalyst for bulky molecular hydrocarbon conversions.

That which is claimed is:

1. A method for preparing zeolite beta which method comprises crystallization of zeolite beta from a solution consisting essentially of a template, a silicon source and an aluminum source in which the template is a polymeric compound comprising a ionizable polydiallyldimethylammonium (PDADMA) cation.

2. A method according to claim 1, wherein the zeolite beta is prepared by hydrothermal crystallization of a solution comprising PDADMA and a silicon source which are present in a molar ratio $SiO_2$/PDADMA between the silicon source calculated as $SiO_2$ and the polymeric compound calculated as the cationic PDADMA monomer is 1-10, the molar ratio $SiO_2/M_2O$ between the silicon source calculated as $SiO_2$ and the base source calculated as alkali metal oxide $M_2O$ is of 1-10.

3. A method according to claim 1, wherein the hydrothermal crystallization is carried out at a temperature of 150-230° C.

4. The method according to claim 1, wherein the molar ratio $SiO_2/Al_2O_3$ between the silicon source calculated as $SiO_2$ and the aluminum source calculated as $Al_2O_3$ is of 20-100.

5. The method of claim 1, comprising dissolving the aluminum source and the base source in the water, adding the polymeric PDADMA compound and stirring for a time period of 0.2-1.5 h.

6. The method of claim 1, wherein the product obtained by crystallization is filtered, dried and calcined sequentially to obtain a final zeolite beta with a composite pore structure.

7. The method of claim 1, wherein the templating polymeric PDADMA compound has a molecular weight of $1 \times 10^5$-$5 \times 10^5$.

8. The method of claim 1, wherein the templating polymeric PDADMA compound is PDADMA salt.

9. The method of claim 8, wherein the templating PDADMA salt is added to the preparation solution in the form of an aqueous solution with a solid content of 10-60 wt %.

10. A hydroconversion catalyst, comprising from 5 to 95 wt % zeolite beta prepared by crystallization of zeolite beta from a solution comprising a template, a silicon source and an aluminum source in which the template is polymeric compound comprising ionizable polydiallyldimethylammonium (PDADMA) cation; from 5 to 95 wt % refractory oxide binder; and from 0.01 to 30 wt % catalytically active metal, wherein the percentages are based on the total dry weight of the catalyst.

11. A hydrocarbon conversion process, which comprises contacting hydrocarbon compounds with the hydroconversion catalyst of claim 10 and hydrogen at a reaction temperature in the range of from 250 to 500° C. and reactor inlet pressure in the range of from $3 \times 10^6$ to $3 \times 10^7$ Pa.

12. The process of claim 11, wherein the hydrocarbon conversion process is chosen from the group consisting of pyrolysis of polyethylene, alkylation of benzene with benzyl alcohol (ABB), condensation of benzaldehyde with hydroxyacetophenone (CBH), and alkylation of phenol with tert-butyl alcohol (APT).

13. The hydroconversion catalyst according to claim 10, wherein the zeolite beta is prepared by hydrothermal crystallization of a solution comprising PDADMA and a silicon source which are present in a molar ratio $SiO_2$/PDADMA between the silicon source calculated as $SiO_2$ and the polymeric compound calculated as the cationic PDADMA monomer is 1-10, the molar ratio $SiO_2/M_2O$ between the silicon source calculated as $SiO_2$ and the base source calculated as alkali metal oxide $M_2O$ is of 1-10.

14. The hydroconversion catalyst according to claim 10, wherein the hydrothermal crystallization is carried out at a temperature of 150-230° C.

15. The hydroconversion catalyst according to claim 10, wherein the molar ratio $SiO_2/Al_2O_3$ between the silicon source calculated as $SiO_2$ and the aluminum source calculated as $Al_2O_3$ is of 20-100.

16. The hydroconversion catalyst according to claim 10, comprising dissolving the aluminum source and the base source in the water, adding the polymeric PDADMA compound and stirring for a time period of 0.2-1.5 h.

17. The hydroconversion catalyst according to claim 10, wherein the product obtained by crystallization is filtered, dried and calcined sequentially to obtain a final zeolite beta with a composite pore structure.

18. The hydroconversion catalyst according to claim 10, wherein the templating polymeric PDADMA compound has a molecular weight of $1 \times 10^5$-$5 \times 10^5$.

19. The hydroconversion catalyst according to claim 10, wherein the templating polymeric PDADMA compound is PDADMA salt.

20. The hydroconversion catalyst according to claim 19, wherein the templating PDADMA salt is added to the preparation solution in the form of an aqueous solution with a solid content of 10-60 wt %.

* * * * *